US007037879B2

(12) United States Patent
Imada et al.

(10) Patent No.: US 7,037,879 B2
(45) Date of Patent: May 2, 2006

(54) PEST CONTROL METHOD FOR GRASS FAMILY PLANTS USING ENDOPHYTIC BACTERIA, PEST CONTROL MATERIAL, AND SEED BOUND TO THE PEST CONTROL MATERIAL

(75) Inventors: Takahiro Imada, Fujinomiya (JP); Naoya Hiruma, Fujinomiya (JP); Tsuyoshi Isawa, Moriya (JP); Munehiro Noda, Fujinomiya (JP); Yohsuke Kurihara, Fujinomiya (JP); Madoka Kon, Fujinomiya (JP)

(73) Assignee: Society for Techno-Innovation of Agriculture Forestry Fisheria and Mayekawa Mfg. Co., Ltd., Tokyo (JP)

( * ) Notice: Subject to any disclaimer, the term of this patent is extended or adjusted under 35 U.S.C. 154(b) by 146 days.

(21) Appl. No.: 10/139,063

(22) Filed: May 2, 2002

(65) Prior Publication Data

US 2003/0195117 A1    Oct. 16, 2003

(30) Foreign Application Priority Data

Apr. 10, 2002 (JP) .............................. 2002-108618

(51) Int. Cl.
*A01N 63/00*     (2006.01)
*C12N 1/20*      (2006.01)

(52) U.S. Cl. ................................... 504/117; 435/252.1
(58) Field of Classification Search ................ 504/117; 435/252.1
See application file for complete search history.

(56) References Cited

U.S. PATENT DOCUMENTS

| | | | |
|---|---|---|---|
| 3,704,546 A | 12/1972 | Hardy et al. | |
| 5,415,672 A | 5/1995 | Fahey et al. | 47/57.6 |
| 5,880,343 A | 3/1999 | Hiruma et al. | 800/320 |
| 5,914,107 A | 6/1999 | Hiruma et al. | 424/93.5 |
| 5,916,029 A | 6/1999 | Smith et al. | 47/57.6 |
| 5,994,117 A * | 11/1999 | Bacon et al. | 435/252.5 |
| 6,103,228 A * | 8/2000 | Heins et al. | 424/93.462 |
| 6,180,855 B1 | 1/2001 | Hiruma et al. | 800/320 |
| 6,261,996 B1 | 7/2001 | Klittich et al. | 504/100 |
| 6,423,499 B1 | 7/2002 | Song et al. | |
| 2001/0032343 A1 | 10/2001 | Hiruma et al. | 800/320 |
| 2002/0040487 A1 | 4/2002 | Imada et al. | 800/278 |
| 2002/0142917 A1 | 10/2002 | Triplett et al. | |
| 2004/0116291 A1 | 6/2004 | Triplett et al. | |

OTHER PUBLICATIONS

Elbeltagy et al. "Endophytic colonization and In Planta Nitrogen Fixation by a *Herbaspirillum* sp. Isolated from Wild Rice Species." Applied and Environmental Microbiology. 67(11):5285-5293. Nov. 2001.*

Siddiqui, Z. A. and Mahmood, I., "Role Of Plant Symbionts In Nematode Management: A Review," *Bioresource Technology*, 54:217-226, 1995.

U.S. Appl. No. 10/139,665, filed May 2, 2002, Tsuyoshi et al.

Alberts et al, Molecular Biology of the Cell, Garland Publishing, pp. 21 and 38, 1995.

Schardl et al, "Protective Grass Endophytes," Plant Diseases, vol. 81, No. 5, 1997. pp. 430-438.

Hallman et al, "*Bacterial endophytes* in agricultural crops," Can. J. Microbiol., vol. 43, 1997, pp. 895-914.

Azevedo et al, "Endophytic microorganisms: a review of insect control and recent advances on tropical plants," Electronic Journal of Biotechnology, vol. 3, No. 1, Apr. 15, 2000, pp. 40-65.

Gopalaswamy Ganesan et al. The xylem of rice is colonized by Azorhizobium caulinodans. Proceedings of the Royal Society Biological Sciences Series B, 267, no. 1439, pp. 103-107, 2000.

Reddy, P. et al. Rhizobia communication with rice roots: induction of phenotypic changes, mode of inveasion and extent of colonization. Plant Soil, 194, pp.115-122,1997.

Webster, G. et al. Interactions of rhizoba with rice and wheat. Plant Soil, 194, pp. 115-122, 1997.

Kirchof G. et al. Occurrence, physiological and molecular analysis of endophytic diazotrophic bacteria in gramineous energy plants- Opportunities for biological nitrogen fixation in rice and other non-legumes. Plant and Soil, 194L, pp.45-55, 1997.

Stoltzful et al., Isolation of endophytic bacteria from rice and assessment of their potential for supplying rice with biologically fixed notrogen. Plant and Soil, 194L, pp. 25-36, 1997.

Mehnaz S. et al. Isolation and 16S rRNA sequence analysis of the beneficial bacteria from the rhizosphere of rice. Canadian Journal of Microbiology, 47 (2), pp. 110-117, 2001.

Egener et al. Use of green fluroscent protein to detect expression of nif genes of Azoarcus sp. BH72, a grass-associated diazotroph, on rice roots. Molecular Plant Microbe Interactions, 11 (1), pp. 71-75, 1998.

Tirol-Padre et al. A plant sampling procedure for acetylene reduction assay to detect rice varietal differences in ability to stimulate N2 fixation. soil Biol. Biochem., 20 (2), pp. 175-183, 1988.

* cited by examiner

*Primary Examiner*—S. Mark Clardy
(74) *Attorney, Agent, or Firm*—Morgan & Finnegan, LLP; Kenneth H. Sonnenfeld; Michael A. Willis

(57) ABSTRACT

The objective of the present invention is to confer pest resistance to plants of Poaceae without using any chemically synthesized pesticides. The pest resistance can be conferred to plants of Poaceae by isolating from a natural plant an endophytic bacterium capable of expressing pest resistance, artificially culturing the endophytic bacterium, and introducing the bacteria to a Poaceae plant of interest.

9 Claims, 1 Drawing Sheet

PEST CONTROL METHOD FOR GRASS FAMILY PLANTS USING ENDOPHYTIC BACTERIA, PEST CONTROL MATERIAL, AND SEED BOUND TO THE PEST CONTROL MATERIAL

FIELD OF THE INVENTION

The present invention relates to a pest control method for grass family (Poaceae) plants using endophytic bacteria, pest control material using the endophytic bacteria, and seeds bound to the pest control material. Particularly, the present invention relates to a biological pest control method for plants of Poaceae, pest control material, and seeds bound to the pest control material, which use endophytic bacteria capable of expressing pest resistance by introducing endophytic bacteria to plants of Poaceae and infecting the plants with the bacteria.

BACKGROUND OF THE INVENTION

Grass family (Poaceae) plants are the most useful plants to human beings. These plants are cultivated and used all over the world, and include: the three major crop plants, namely, rice, wheat, and corn; sorghum, which is the staple food in African countries and India; pasture grass for livestock feed; and turf grass used for parks, playing fields, golf courses, green fields, etc. The most serious problem encountered in the cultivation of plants of Poaceae used in such various fields is damage caused by harmful pests.

Various methods have been developed so far to control pests. Among them, the most commonly used and the most developed method is the chemical control method using chemical pesticides. Chemical pesticides are convenient to use and have immediate effects to protect plants from pests, but are listed as specified poisonous substances, poisonous substances, deleterious substance, etc., which are regulated by law. In recent years, the abuse of chemical pesticides have created social problems: intoxications and deaths caused by acute toxicity; contamination of food due to residual pesticides in agricultural products; and influence of the outflow of residual pesticides on the human body and environment. Furthermore, new pests resistant to previous chemical pesticides are emerging, forcing the development of new types of pesticides, creating an endless cycle.

SUMMARY OF THE INVENTION

As a measure to protect the environment, efforts are being made to develop new biological control methods that have little impact on the environment. There are various plant-breeding technologies that confer pest resistance to plants themselves, such as artificial mating, selection, mutagenesis, cell fusion, gene transfer, and so on. Among them, the gene transfer method is used very widely. For example, maize and rice plants introduced with a gene such as the one encoding the above-mentioned pesticidal toxin protein derived from *Bacillus thuringensis* (*B.t.*) have been created. Furthermore, a variety of dent corn for livestock feed to which the gene has been introduced is actually being cultivated.

However, pesticidal proteins such as the *B.t.* toxin affect not only target pests, but also a wide range of harmless organisms. There is a report that describes that Monarch butterflies (*Danaus plexippus*) died after having eaten pollen of maize that contains the introduced gene encoding the pesticidal protein *B.t.* toxin. Thus, pesticidal proteins carry the risk of disrupting the natural environmental.

There is also another biological control method, which utilizes microorganisms or enemy insects in the natural world. Examples are: the use of microorganisms competitive to pathogenic microorganisms; use of the above-mentioned pesticidal protein toxin derived from *Bacillus thuringensis* (*B.t.*), or the like; and use of predatory insects that are the natural enemies of pests. The majority of microorganisms competitive to pathogenic microorganisms are competitive to pathogenic microorganisms in soil. However, there is no application of microorganisms competitive to pathogenic microorganisms, such as the rice blast fungus that invades and affects plants through directly attaching its spores to the leaves and stem. *B.t.* toxin cannot be used for pests belonging to *Lepidoptera* for preventive purposes, since this toxin is used after the pests are detected. Thus, it is effective only when properly used while closely monitoring pest occurrence. The use of natural enemies is effective when pests break out in covered cultivations such as in greenhouses, but are hardly usable in pest outbreaks in open-air cultivations, such as for plants of Poaceae.

In nature, there are endosymbiotic microorganisms, namely endophytes, which live in plants. The endophytes inhabit plant tissues, in particular, spaces between cells called intercellular spaces. It has previously been reported that plants of Poaceae infected with endophytic filamentous fungi belonging to the genus Neotyphodium exhibit improved resistance to pests, pathogenic microorganisms, and environmental stresses such as heat and drought, and also improved growing rates compared to uninfected plants.

Plants infected with symbiotic endophytes have the above-mentioned resistance conferred by the endophytes. Therefore, no pesticides are required for cultivating these plants, which means that prevention is possible no matter what pest occurrences have been predicted. Furthermore, it is a technology that uses the laws of nature, and thus, neither gives harmful side effects as those with plants containing introduced genes, nor affects other plant phenotypes.

Endophytes are categorized roughly into the two groups of filamentous fungi and bacteria. Filamentous fungal endophytes have been used for plants of Poaceae, namely for plants to which *Neotyphodium* infects and lives symbiotically in. However, filamentous fungal endophytes show host specificity; the host plants that they can infect and live symbiotically in are limited to a narrow range of related species. Thus, fungal endophytes can be used only for pasture grass and turf grass species.

Practically used symbiotic bacterial endophytes are only root nodule bacteria, such as *Rizobium, Bradyrhizobium, Mesorhizobium*, and *Sinorhizobium*, which live producing root nodules on the roots of plants of Leguminosae by fixing and supplying atmospheric nitrogen to the plants.

There are some reports that describe finding symbiotic bacterial endophytes that fix nitrogen in sugarcane or rice plant belonging to Poaceae. However, there is no endophytic bacterium capable of conferring pest resistance to Leguminosae or Poaceae plants.

The present invention was made considering these problems, and the objective is to provide a biological control method using endophytic bacteria-introduced plants. The instant method comprises artificially introducing to a plant endophytic bacteria capable of infecting and living symbiotically the plant, thus conferring pest resistance to the plant; a pest control material; and seeds bound to the pest control material.

The present invention mainly relates to a pest control method for plants belonging to the family of Poaceae, which comprises infecting a plant of Poaceae with endophytic bacteria by artificially introducing the bacteria into the plant, and thus conferring pest resistance to the plant via the above-mentioned endophytic bacteria.

Thus, resistance to diseases caused by bacteria, or filamentous fungi, can be conferred to Poaceae plants by artificially introducing the endophytic bacteria to the plants. Further, resistance to pests belonging to *Lepidoptera, Orthoptera, Thysanoptera, Coleoptera*, or *Hemiptera* can be conferred to Poaceae plants by artificially introducing endophytic bacteria to the plants. It is preferred that the endophytic bacteria used for this purpose belong to the genus *Herbaspirillum* or the genus *Azospirillum*.

Further, it is preferred that the endophytic bacteria is one or more of the bacteria deposited in the National Institute of Bioscience and Human-Technology under the accession numbers of FERM P-18563 (converted to accession number FERM BP-10395), FERM P-18564 (converted to accession number FERM BP-10447), FERM BP-7998, FERM BP7999, and FERM BP8000. The endophytic bacteria inhabit intercellular spaces in a plant, and confer pest resistance to the plant. Accession number FERM BP-10395 was converted on Aug. 5, 2005 from accession number FERM P-18563, which was deposited on Oct. 18, 2001 at the National Institute of Advanced Industrial Science and Technology. Accession number FERM BP-10447 was converted on Nov. 9, 2005 from accession number FERM P-18564, which was deposited on Oct. 18, 2001 at the National Institute of Advanced Industrial Science and Technology. Accession number FERM BP-7998, described as *Herbaspirillum* sp. MYK-B001 was deposited on Apr. 4, 2002 at the National Institute of Advanced Industrial Science and Technology. Accession number FERM BP-7999, described as *Herbaspirillum* sp. MYK-B002 was deposited on Apr. 4, 2002 at the National Institute of Advanced Industrial Science and Technology. Accecssion number FERM BP-8000, described as *Azospirillum* sp. MYK-B003 was deposited on Apr. 4, 2002 at the National Institute of Advanced Industrial Science and Technology. The National Institute of Advanced Industrial Science and Technology has an address of AIST Tsukuba Central 6, 1-1, Higashi 1-chome, Tsukuba-shi, Ibaraki-ken 305-8566, Japan.

The plant to which the endophytic bacteria are to be artificially introduced is a plant of Poaceae of any one of *Agegilop, Agrostis, Avena, Axonopus, Buchloe, Coix, Cynodon, Dactylis, Eragrostis, Eremochloa, Festuca, Hordeum, Lolium, Oryza, Paspalum, Pennisetum, Phleum, Poa, Saccharum, Secale, Sorghum, Stenotaphrum, Triticum, xTriticosecala, Zea*, and *Zoysia*. Further, the plant includes also hybrids between the above.

The present invention also relates to a pest control method for plants of Poaceae, which comprises the steps of isolating from a natural plant an endophytic bacterium capable of expressing pest resistance, artificially culturing the isolated endophytic bacterium, introducing the artificially cultured endophytic bacteria into a plant of interest, and infecting the plant with the introduced endophytic bacteria.

Thus, a bacterium can be isolated by grinding a plant that is assumed to contain the endophytic bacterium, inoculating the processed products into a culture medium, and culturing the bacterium. The endophytic bacteria can be introduced into seeds or plants that germinate from the seeds by contacting seeds of an above-mentioned plant of Poaceae with an aqueous solution in which the endophytic bacteria have been dispersed. The aqueous solution in which the endophytic bacteria are dispersed is preferably physiological saline. It is preferable to introduce the above-mentioned endophytic bacteria into seeds or plants that germinate from the seeds by dispersing the above-mentioned endophytic bacteria in a seed-soaking solution that is used in seed soaking prior to seeding.

Further, it is preferred that DNA of the isolated endophytic bacterium is amplified by PCR and the bacterium is identified by carrying out a homology search for the DNA amplified. Further, it is preferred that a foreign gene that expresses an identifiable means is introduced into the above-mentioned endophytic bacterium, and the presence of colonization of the above-mentioned endophytic bacterium infecting the plant is confirmed by the above-mentioned identifiable means using the foreign gene.

A major invention regarding pest control materials relates to a material comprising as its main ingredient endophytic bacteria isolated from a natural plant, which provides pest resistance to a plant of Poaceae when the bacteria are artificially introduced to the plant.

It is preferred that the endophytic bacteria belong to the genus *Herbaspirillum* or the genus *Azospirillum*. Further, it is preferred that the endophytic bacteria are one or more of the bacteria deposited in the National Institute of Bioscience and Human-Technology under the accession numbers of FERM P-18563, FERM P-18564, FERM BP-7998, FERM BP-7999, and FERM BP-8000. Further, the endophytic bacteria may be dispersed in a binding agent, and the binding agent may serve as a seed-coating layer. Further, when artificially introduced into a plant, the endophytic bacterium may express resistance to diseases caused by bacteria or filamentous fungi. Alternatively, when introduced artificially into a plant, the endophytic bacteria may express resistance to pests belonging to the *Lepidoptera, Orthoptera, Thysanoptera, Coleoptera*, or *Hemiptera*.

A major invention regarding seeds relates to a seed bound to a coating agent that is prepared by a method that comprises dispersing endophytic bacteria, which confer pest resistance when introduced into a plant of Poaceae, in the binding agent used for seed-coating.

It is preferred that the endophytic bacteria belong to the genus *Herbaspirillum* or the genus *Azospirillum*. Further, it is preferred that the endophytic bacteria are one or more of the bacteria deposited in the National Institute of Bioscience and Human-Technology under the accession numbers of FERM P-18563, FERM P-18564, FERM BP-7998, FERM BP-7999, and FERM BP-8000. In addition, it is preferred that the above-mentioned binding agent is carbide (calcium carbonate).

The present invention focused on endophytic bacteria that confer pest resistance to plants that have been infected with and allowed to live in symbiosis with the bacteria. Thus, the present invention comprises artificially introducing such endophytic bacteria into a plant, screening the endophytic bacteria prior to the introduction or screening the plants living in symbiosis after the introduction, and achieving the infection. In particular, it was confirmed that bacteria belonging to the genus *Herbaspirillum* or the genus *Azospirillum* were effective as endophytic bacteria that infect and live symbiotically in plants of Poaceae.

It was confirmed that all endophytes found and cultured by the present inventors, particularly, *Herbaspirillum* sp. strains MYK-B001 and MYK-B002 (deposited in the National Institute of Bioscience and Human-Technology under the accession numbers of FERM P-7998 and FERM P-7999) and *Azospirillum* sp. strain MYK-B003 (deposited in the National Institute of Bioscience and Human-Technology under the accession number of FERM P-8000) can be introduced into various Poaceae plants, and live in symbiosis with the plants. It was also found that these endophytes could confer pest resistance to the introduced infected plants. Endophytes may be introduced to any one of the plants of *Agegilop, Agrostis, Avena, Axonopus, Buchloe, Coix, Cynodon, Dactylis, Eragrostis, Eremochloa, Festuca, Hordeum, Lolium, Oryza, Paspalum, Pennisetum, Phleum, Poa, Saccharum, Secale, Sorghum, Stenotaphrum, Triticum, xTriticosecala, Zea,* and *Zoysia,* including the progenies and hybrids between the above.

The method for introducing bacterial endophytes is descried below. This method comprises isolating endophytes that live symbiotically in nature plants and artificially culturing them. Then, the artificially cultured endophytes are artificially inoculated to Poaceae plants. The endophytes inoculated artificially are introduced into Poaceae plants by infecting the plants with the endophytes and allowing the bacteria to live in symbiosis. The endophytes are selected by screening prior to artificial inoculation to plants or after the artificial inoculation.

Any one of the above-mentioned endophytes deposited in the National Institute of Bioscience and Human-Technology may be used for the step of artificial inoculation. Further, the endophyte introduced is not always a single type of endophyte; two or more types of endophytes may be introduced simultaneously or successively.

The present inventors achieved the colonization of *Herbaspirillum* sp. strains MYK-B001 and MYK-B002, and *Azospirillum* sp. strain MYK-B003 in Poaceae plants by inoculating them to the plants. Then, they tested the respective plant species for pests, and found that all the endophyte-infected plants exhibited strong resistance to pests as well as to diseases, while the endophyte-uninfected plants were affected with diseases and were eaten by pests.

This finding indicates that pest resistance can be almost permanently conferred by infecting a plant of Poaceae with an endophyte once and allowing the endophyte to live symbiotically in the plant. Thus, plants can be cultivated without chemical pesticides conventionally used for pest control. In addition, as compared to other biological control methods, this method enables a sharp reduction of pest occurrence prediction costs, the need to evaluate the use of a pest control method depending on pest occurrence status, and the need to study the impact on the environment, etc. Thus, it is possible to reduce cultivation costs as well as adverse influences on the environment.

DETAILED DESCRIPTION OF THE INVENTION

Figure 1:
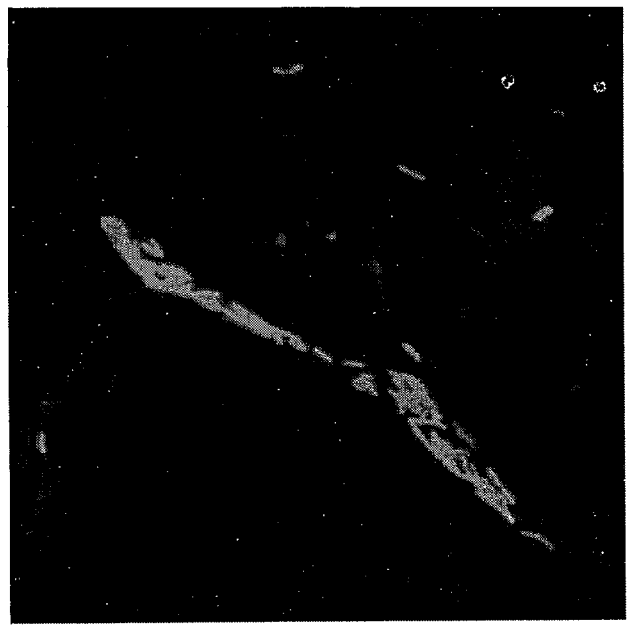
FIG. 1 is a photomicrograph of a plant to which endophytic bacteria have been introduced.

The procedures of the pest control method according to the present invention, which comprises introducing endophytes to plants of Poaceae, is described below in detail.

Stage 1. Isolation of Endophytes (1) Isolation and Culture of Endophytes

Endophytes are isolated as follows: Pieces of naturally growing plants are collected are sterilized; the pieces are ground before or after sterilization, then plated on an endophyte-isolation medium and cultured for a few days to isolate the endophytes.

(2) Identification of Endophytes

The bacteria are isolated from single colonies on the culture medium and identified by analyzing their 16s rRNA genes.

(3) Labeling of Endophytes

After the species are identified, if required, aliquots of the endophytes are labeled with GFP to enable the verification of infection within plants after inoculation.

Stage 2. Introduction of Endophytes

The isolated endophytes are artificially introduced into any Poaceae plant of interest belonging to the genus *Agegilop, Agrostis, Avena, Axonopus, Buchloe, Coix, Cynodon, Dactylis, Eragrostis, Eremochloa, Festuca, Hordeum, Lolium, Oryza, Paspalum, Pennisetum, Phleum, Poa, Saccharum, Secale, Sorghum, Stenotaphrum, Triticum, xTriticosecala, Zea,* and *Zoysia.* Methods for introducing endophytes include: an inoculation method comprising adhering endophytes to seeds; a method comprising coating seeds with endophytes; and a method comprising directly inoculating endophytes to plants. An appropriate method may be chosen depending on the type of plant to which the endophyte is to be introduced.

Particularly, when the method comprising adhering endophytes to seeds is used, the inoculation can be achieved simply by dispersing the isolated symbiotic bacterium, namely endophyte, in physiological saline, and contacting seeds with the bacteria-dispersed physiological saline. Namely, the inoculation may be achieved by pouring the bacteria-dispersed physiological saline on seeds or soaking seeds in the bacteria-dispersed physiological saline.

Particularly, when one intends to contact the endophyte with unhulled rice, which is the seed of cultivated rice plant belonging to Poaceae plants, the inoculation can be achieved at the time of seed soaking before seeding. Namely, the endophytic bacteria are dispersed in the soaking solution used in soaking of unhulled rice, and then the unhulled rice is soaked in the solution. Thus, seeds or plants that germinate from the seed are infected with the bacteria contained in the soaking solution.

Alternatively, seeds of various crops belonging to Poaceae plants can be coated with a pest control material comprising the above-mentioned endophytic bacterium. In this case, it is preferred that the above-mentioned coating layer is formed by using a binding agent comprising carbide (calcium carbonate).

Stage 3. Confirmation of Endophyte Introduction

The infection of endophytes can be confirmed by observing gfp gene-introduced plant tissue pieces under a fluorescence microscope. Further, the introduced endophytes are separated by plating the tissue on an NB medium after sterilizing the tissue surface.

Stage 4. Test of Endophyte-Introduced Plants (1) Insect-Resistance Test

Insect resistance can be assessed by conducting an artificial insect damage test comprising breeding pests of interest using endophyte-introduced symbiotic plants and plants without endophytes.

(2) Disease-Resistance Test

A pathogenic microorganism of interest is artificially cultured and artificially inoculated to endophyte-introduced symbiotic plants and plants without endophytes, to cause a disease. Disease resistance can be assessed by measuring the extent of disease in each plant.

A major invention described herein comprises artificially introducing and thus infecting plants of Poaceae with endophytic bacteria and thereby conferring pest resistance to the plants via the above-mentioned endophytic bacteria.

Thus, by such a pest control method, resistance to pest damage is conferred to plants that are artificially infected with endophytic bacteria to form a symbiosis. Thus, the introduced endophytic bacteria confer the same pest resistance as achieved by conventional pesticides. This enables the reduction of the amount of chemically synthesized pesticides used, and overcomes the problems of biological pesticides that have poor effects, while reducing environmental damages and costs for cultivating Poaceae plants though the use of biological protection.

Another major invention described herein comprises the steps of isolating an endophytic bacterium capable of expressing pest resistance from natural plants; artificially culturing the isolated endophytic bacterium; introducing the artificially cultured bacteria into plants of interest; and infecting plants with the introduced endophytic bacteria.

Thus, such pest control method enables one to highly reproducibly introduce bacteria conferring pest resistance to the plants of Poaceae, and infect the plants with the bacteria. The plants of Poaceae can exhibit pest resistance, through such endophytic bacteria. Thus, this method makes it possible to minimize the amount of chemically synthesized pesticides used and provides Poaceae plants having little environmental burden due to the use of biological protection.

A major invention regarding a pest control material relates to a material comprising as its main ingredient an endophytic bacterium isolated from a natural plant, which provides pest resistance to a plant of Poaceae by artificially introducing the bacterium into the plant.

Thus, pest resistance can be conferred Poaceae plants by applying such a pest control material. This makes it possible to minimize the amount of chemically synthesized pesticides used, cultivation costs, and environmental damage.

A major invention regarding seeds comprises coating plant seeds with a binding agent comprising a suspension of endophytic bacteria conferring pest resistance to Poaceae plants when introduced into the plants.

Thus, when a seed bound to such a pest control material are disseminated, endophytic bacteria are introduced into and infect plants that germinate and grow from the seed since endophytic bacteria dispersed in the binding agent adhere to the outer coating-layer of the seed.

EXAMPLE 1

(1) Isolation of Endophytes

Plants of Poaceae grown in natural soils were collected at random. The plants were chopped and soaked in 70% ethanol for 30 seconds, and then in 2% sodium hypochlorite for 5 minutes for surface sterilization. Then, the plants were ground in a mortar while adding sterilized physiological saline and sea sand. The products were inoculated to an NB medium, and then cultured at 30° C. for a few days under darkness. Then, single colonies formed on the culture medium were isolated.

(2) Identification of Endophytes

The nucleotide sequence of the 16s rRNA gene was determined after amplifying by PCR. Several types of forward and reverse internal primers in the 16S rRNA gene were prepared. From them, a pair of primers was selected, and PCR was carried out using, as a template, DNA extracted from the lysed bacterial cells. The amplified DNA fragment was purified by removing salts and primers, and then the nucleotide sequence was determined. The nucleotide sequence of approximately 1.5-kb segment in the 16s rRNA gene was determined. The determined nucleotide sequence was searched for homology against the DDBJ/GenBank/EMBL databases.

Then, the phylogenetic relationship of the strains and other bacterial species was analyzed with the program ClastalW, which had been used to construct the phylogenetic trees. The nucleotide sequences used for the analysis were: the determined nucleotide sequences for the newly identified strains; the nucleotide sequences of 16s rRNA genes of bacteria belonging to genera or species, which exhibited high homology to the determined sequences; and the nucleotide sequences of 16s rRNA genes from a wide variety of bacterial genera and species in addition to the above. Based on this analysis, a phylogenetic tree was constructed. The result showed that the strains MYK-B001 and MYK-B002 belonged to the genus *Herbaspirillum*, and the strain MYK-B003 belonged to the genus *Azospirillum*.

(3) Preparation of Labeled Bacteria

Since it is difficult to observe the introduced endophytes, namely bacteria, in plant tissues, a gene encoding a self-fluorescent protein was integrated into the bacteria. GFP (Green Fluorescent Protein) is a protein isolated from the jellyfish *Aequoria Victoria*. When irradiated by blue or ultraviolet light, the protein emits a green fluorescent light. The gene for GFP, namely gfp gene, can be used to label cells of isolated strains. There is a plasmid, called pUTg-fpx2, which is a mini-transposon comprising two units of the gfp gene and kanamycin resistance gene integrated in the plasmid pUT that replicates only in bacteria belonging to *Enterobacteriaceae*. This plasmid was introduced into cells of, for example, *Herbaspirillum* sp. strains MYK-B001 and MYK-B002, by electroporation, and then kanamycin-resistance bacteria were isolated. It was confirmed that these bacterial cells emitted fluorescent light upon irradiation of light around 500 nm.

(3) Culture of Bacterial Strains

*Herbaspirillum* sp. strains MYK-B001 and MYK-B002, and *Azospirillum* sp. strain MYK-B003 were cultured by the same method. Single colonies of the strains were inoculated to the NB culture media. The cells were incubated at 30° C. while being shaken.

(4) Inoculation to the Plants of Poaceae

1. Inoculation of Adhesive Bacteria to Seeds

After culturing in NB media, bacterial cells in the logarithmic growth phase were harvested by centrifugation at 8000 G (G: gravity) for 1 minute. The bacterial cells were washed by repeating 3 times the step of suspending them in physiological saline and harvesting. The washed bacterial cells were suspended in physiological saline at the cell density of $2 \times 10^7$ cells/ml. After removing the hulls, the plant seeds were soaked in 70% ethanol for several seconds, and then immediately washed with sterilized water. The seeds were shaken in an aqueous solution of 2.5% sodium hypochlorite for 30 minutes for surface sterilization, and then washed by repeating 3 times the step of shaking them in sterilized water for 15 minutes. Red ball soil and seedling-raising soil (trade name: Coop Ube Glandular Cultivation Soil (National Federation of Agricultural Co-operative Associations)), which had been pre-sterilized by autoclaving at 121° C. for 15 minutes, were combined at a ratio of 1:3 and the surface-sterilized seeds were placed in a plant box or test tube containing the mixed soil. Bacterial inoculation was achieved by placing, for example, a 50 μl drop of the above-mentioned bacterial suspension ($1 \times 10^6$ cells) on a seed. Lists of the plant species of Poaceae inoculated here are shown in Tables 1 and 2.

2. Bacterial Inoculation to Seeds Through Coating

After culturing in NB media, bacterial cells in the logarithmic growth phase were harvested by centrifugation at 8000 G (G: gravity) for 1 minute. The bacterial cells were washed by repeating 3 times the step of suspending them in physiological saline and harvesting. The washed bacterial cells were suspended in physiological saline at the cell density of $1 \times 10^6$ cells/ml. Bacterial inoculation was achieved by seed-coating with bacteria, for example, using the bacterial suspension and carbide (calcium carbonate ($CaC_2$)). Lists of the plant species of Poaceae inoculated here are shown in Tables 1 and 2.

3. Bacterial Inoculation to Plants by Spraying with a Bacterial Suspension

Seeds were sown in vinyl pots containing red ball soil and seedling-raising soil (trade name: Coop Ube Glandular Cultivation Soil (National Federation of Agricultural Co-operative Associations)) mixed at a ratio of 1:3. Then, the plant was grown until second leaves developed in a culture room under conditions of a 16-hour light period and an 8-hour dark period at 25° C. for 10 days.

After culturing in NB media, bacterial cells in the logarithmic growth phase were harvested by centrifugation at 8000 G (G: gravity) for 1 minute. The bacterial cells were washed by repeating 3 times the step of suspending them in physiological saline and harvesting. The washed bacterial cells were suspended in physiological saline at the cell density of $1 \times 10^6$ cells/ml.

Then, the spreading agent Tween 20 was added to the prepared bacterial suspension; in the resulting mixture, the agent was diluted 5000 to 10000 times. The bacteria were inoculated evenly to the plants grown to the stage of second leaf development by spraying. Lists of the plant species of Poaceae inoculated here are shown in Tables 1 and 2.

(5) Growth of Endophyte-Infected Plants of Poaceae

1. Cultivation in Plant Boxes or Test Tubes

Red ball soil and seedling-raising soil (trade name: Coop Ube Glandular Cultivation Soil (National Federation of Agricultural Co-operative Associations)) were combined at a ratio of 1:3 and placed in plant boxes or test tubes. The plants, which had been inoculated with *Herbaspirillum* sp. strains MYK-B001 and MYK-B002, and *Azospirillum* sp. MYK-B003 strain, were aseptically cultivated in the soil under the conditions of a 16-hour light period and an 8-hour dark period at 25° C. for 10 to 14 days. Then, the plants were further cultivated non-aseptically under the conditions of a 16-hour light period and an 8-hour dark period at 25° C. for 10 to 14 days.

2. Cultivation in Vinyl Pots

Plants were inoculated with *Herbaspirillum* sp. strains MYK-B001 and MYK-B002, and *Azospirillum* sp. MYK-B003 strain by spraying, and then were cultivated under the conditions of a 16-hour light period and an 8-hour dark period at 25° C. for 10 to 14 days.

3. Cultivation in Wagner Pots

Embryo plants grown in plant boxes or vinyl pots were transplanted into 1/5000-a Wagner pots containing a mixture of red ball soil and seedling-raising soil (trade name: Coop Ube Glandular Cultivation Soil (National Federation of Agricultural Co-operative Associations)) combined at a ratio of 1:3, and cultivated under the conditions of an 11-hour light period at 28° C. and a 13-hour dark period at 22° C. till maturity.

(6) Confirmation of Infection

1. Confirmation of Infection under a Fluorescence Microscope

Plants that had been inoculated with *Herbaspirillum* sp. strains MYK-B001 and MYK-B002 and *Azospirillum* sp. MYK-B003 strain labeled with the GFP gene were observed under a fluorescence stereomicroscope. Further, leaf blades of the plants were observed under a confocal laser microscope to clarify which plant tissues the bacteria had colonized. Many labeled bacterial cells were observed to colonize the aboveground parts and subterranean parts of plants. In plant tissues, the bacteria were found to colonize intercellular spaces (photograph 1). As shown in Tables 1 and 2, the bacteria were found to infect and live in symbiosis with the plants of Poaceae in every combination of plant species and inoculation method tested.

2. Confirmation of Infection by Isolation

Rice plants inoculated with the bacteria were cultivated for 10 to 14 days. The whole embryo plants were surface-sterilized by soaking them in 70% ethanol for several seconds and then in 1% sodium hypochlorite for 30 seconds. After surface sterilization, the plants were ground in a mortar while adding sterilized physiological saline and sea sand. The products were smeared on NB agar plates. The number of colonies generated was counted to evaluate the in-tissue colonization of the inoculated bacteria. The endophytes were isolated, and accordingly, *Herbaspirillum* sp. strains MYK-B001 and MYK-B002, and *Azospirillum* sp. MYK-B003 strain were found to colonize the inoculated plants. As shown in Tables 1 and 2, the bacteria were found to infect and live in symbiosis with the plants of Poaceae in every combination of plant species and inoculation method tested.

EXAMPLE 2

Assessment of Blast-Resistance of Endophyte-Infected Rice Plants (1) Assessment of Resistance to Leaf-blast Disease The usefulness of endophyte-infected rice plants was assessed by testing resistance to blast, which is a major rice plant disease. The endophytes inoculated were: *Herbaspirillum* sp. strains MYK-B001 and MYK-B002, and *Azospirillum* sp. MYK-B003 strain. The bacteria were inoculated to the cultivated rice plant *Oryza Sativa*. The blast fungus (*Ptricularia oryza Cavara*) used was Kita-1 strain (race 003).

After the inoculation of endophytes by the above-mentioned methods, individual plants of the cultivated rice plant *Oryza Sativa* were cultivated to the 4 to 5th leaf stages.

A suspension of spores of the rice blast fungus was prepared by washing the surface of dry spore-forming medium with Tween 20 diluted 5000 to 10000 times with distilled water; the suspension was diluted to adjust the spore density so that 20 to 100 spores were visible when viewed under the hundred fold view field of a microscope. The bacteria were inoculated by spraying evenly to embryo rice plants grown up to the 4 to 5th leaf stages.

The inoculated plants were covered with vinyl bags and incubated under 100% humidity with a humidifier at 25° C. in an incubator for 24 hours to ensure bacterial infection. After 24 hours, the plants were further incubated to develop the disease in the incubator under the conditions: normal humidity of 50 to 60%; 25° C.; 16-hour light period and 8-hour dark period. The leaf having the largest local lesion was defined as the most diseased leaf. The diameter of the local lesion, namely, size of the local lesion, of every individual plant inoculated was measured. The difference in the average value between non-inoculated and endophyte-inoculated plants was calculated by the least significant difference method, to determine the significant difference; when the size of the local lesion was significantly small, the plant was assessed to be resistant to blast fungus.

The plants that had been inoculated with *Herbaspirillum* sp. strain MYK-B001 or MYK-B002, or *Azospirillum* sp. MYK-B003 strain, and non-inoculated plants were compared by a significance test using average blast lesion sizes. Disease onset was suppressed in plants inoculated with *Herbaspirillum* sp. MYK-B002 strain at 1% significance level; *Herbaspirillum* sp. MYK-B001 strain and *Azospirillum* sp. MYK-B003 strain at 5% significance level, when compared to the levels of non-inoculated plants.

The above finding showed that the resistance to leaf blast was conferred to cultivated rice plants *Oryza Sativa* through the infection and symbiosis with the endophytes *Herbaspirillum* sp. strains MYK-B001 and MYK-B002, and *Azospirillum* sp. MYK-B003 strain.

(2) Assessment of Resistance to Ear Blast

Cultivated rice plants *Oryza Sativa* inoculated with *Herbaspirillum* sp. strain MYK-B001 or MYK-B002, or *Azospirillum* sp. MYK-B003 strain, which were also used in the leaf blast test, were transplanted into a 1/5000-a Wagner pot containing red ball soil and seedling-raising soil (trade name: Coop Ube Glandular Cultivation Soil (National Federation of Agricultural Co-operative Associations)) combined at a ratio of 1:3. The plants were cultivated under the conditions of an 11-hour light period at 28° C. and a 13-hour dark period at 22° C. Then, the rice blast fungus was inoculated at the stage of ear emergence. A suspension of spores of the rice blast fungus, the same strain used in the leaf blast test, was prepared by washing the surface of dry spore-forming medium with Tween 20 diluted 5000 to 10000 times with distilled water; the suspension was diluted to adjust the spore density so that 20 to 100 spores were visible when viewed under the hundred fold view field of a microscope. The bacteria were inoculated by spraying evenly to rice plants.

The inoculated plants were covered with vinyl bags and incubated under 100% humidity with a humidifier at 25° C. for 24 hours to ensure bacterial infection. After 24 hours, the plants were further incubated to develop the disease in the incubator under the conditions: normal humidity of 50 to 60%; 25° C.; 16-hour light period and 8-hour dark period.

On the 20th to 30th day after inoculation, observations were made to check the onset of panicle base blast disease, rachis blast disease, and rachis-branch blast disease. The difference in the average value between non-inoculated plants and endophyte-inoculated plants was calculated by the least significant difference method, to determine the significant difference; when the disease frequency was significantly low, the plant was assessed to be resistant to ear blast.

A result similar to that in the leaf blast test was obtained, namely the plants that had been inoculated with *Herbaspirillum* sp. strain MYK-B001 or MYK-B002, or *Azospirillum* sp. MYK-B003 strain, and non-inoculated plants were compared for the blast disease frequency by a significance test. Ear blast was suppressed in plants inoculated with *Herbaspirillum* sp. MYK-B002 strain at 1% significance level; *Herbaspirillum* sp. MYK-B001 strain and *Azospirillum* sp. MYK-B003 strain at 5% significance level, when compared to non-inoculated plants.

The above findings showed that the resistance to leaf blast and ear blast was conferred to cultivated rice plants *Oryza Sativa* through the infection and symbiosis with the endophytes *Herbaspirillum* sp. strains MYK-B001 and MYK-B002, and *Azospirillum* sp. MYK-B003 strain.

In the present embodiment, blast-resistance of the cultivated rice plants *Oryza Sativa* was assessed. The result suggests that disease resistance is conferred to Poaceae plants as a whole through the infection and symbiosis with the endophytes *Herbaspirillum* sp. strains MYK-B001 and MYK-B002, and *Azospirillum* sp. MYK-B003 strain. Thus, it was revealed that the infection and symbiosis with endophytic bacteria could be applied to plants of Poaceae as a biological control method in the cultivation of these plants.

EXAMPLE 3

Assessment of Pest Resistance of Endophyte-infected Plants of Poaceae

Major pests for Poaceae plants are insects belonging to *Orthoptera, Thysanoptera, Hemiptera, Lepidoptera,* and *Coleoptera,* and these insects damage the plants by eating and sucking on the plants. It was assessed whether the resistance to such pests was conferred to the plants through the infection with endophytes.

First, the endophytes were assessed for the effect towards the lawn grass cutworm *Spodoptera depravata* (Butler), which is a major pest insect of the family of cutworms that causes insect damage to every plant of Poaceae.

The endophytes used were *Herbaspirillum* sp. strains MYK-B001 and MYK-B002, and *Azospirillum* sp. MYK-B003 strain. Inoculated plants were prepared and grown by the same method as described above.

The feeding test was carried out as follows: leaf blades of endophyte-inoculated and non-inoculated plants were cut into 20-mm square pieces and then placed in 90-mm dishes; approximately 200 larvae of the lawn grass cutworm *Spodoptera depravata* immediately after hatching were placed therein and allowed to feed in an incubator at 25° C. under the conditions of a 16-hour light period and an 8-hour dark period. After 48 hours, the feeding rate was determined. In addition, 20 third-instar larvae of the lawn grass cutworm *Spodoptera depravata* were placed and allowed to feed in an incubator at 25° C. under the conditions of a 16-hour light period and an 8-hour dark period. After 48 hours, the feeding rate was determined.

The feeding rate during 48 hours of the lawn grass cutworm larvae immediately after hatching was as follows: only 20% for the plants inoculated with *Herbaspirillum* sp. MYK-B001 strain; nearly 100% for the non-inoculated plants and plants inoculated with *Herbaspirillum* sp. MYK-B002 or *Azospirillum* sp. MYK-B003 strain. Thus, there was a significant difference (Photograph 2).

Figure 2:
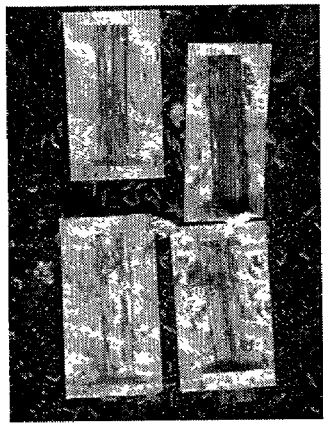
FIG. 2 is a photograph representing a test result using cutworm larvae immediately after hatching.

In the photographic illustration shown in FIG. 2, the plant in the upper left panel was inoculated with *Azospirillum* sp. MYK-B003 strain (FERM BP-8000); upper right, inoculated with *Herbaspirillum* sp. MYK-B001 strain (FERM BP-7998); left bottom, with *Herbaspirillum* sp. MYK-B002 strain (FERM BP-7999); right bottom, the non-inoculated control plant, respectively.

Further, the result of a feeding test using 20 third-instar larvae of the lawn grass cutworm *Spodoptera depravata* showed that the plant inoculated with *Herbaspirillum* sp. MYK-B001 strain was barely eaten during 48 hours from the start of test; the feeding rate was only 5% (Photograph 3). All the non-inoculated plants, plant inoculated with *Herbaspirillum* sp. MYK-B002 strain or *Azospirillum* sp. MYK-B003 strain were eaten and the rates were very similar to one another.

Figure 3:
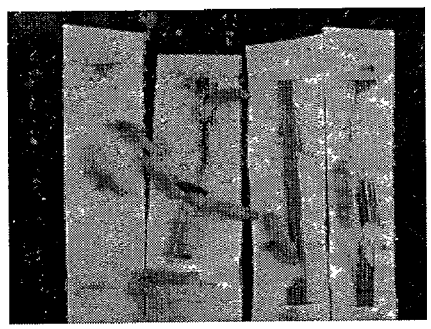
FIG. 3 is a photograph representing a test result using third-instar cutworm larvae.

In the photographic illustration of FIG. 3, the plant shown in the left panel was inoculated with *Azospirillum* sp. MYK-B003 strain (FERM BP-8000); the one shown in the second panel from left is a non-inoculated control; the one in the second panel from right was inoculated with *Herbaspirillum* sp. MYK-B001 train (FERM BP-7998); the one in the right panel was inoculated with *Herbaspirillum* sp. MYK-B002 strain (FERM BP-7999), respectively.

Likewise, the endophyte exhibited inhibiting effects to pests that feed on other plants.

These findings shown above indicate that the endophyte *Herbaspirillum* sp. MYK-B001 strain confers strong insect resistance to the plants of Poaceae that are infected with and that live in symbiosis with this bacterium, and also confers resistance to pests belonging to *Lepidoptera* including similar cutworms, pests of *Orthoptera* such as grasshoppers, etc.

Further, it was revealed that endophytes showed inhibiting effects, such as an aversion effect, in a test using plant-sucking pests belonging to the *Hemiptera* including leafhoppers and stinkbugs. Thus, it was revealed that the infection and symbiosis with endophytic bacteria could be applied to plants of Poaceae as a biological control method in the cultivation of these plants.

TABLE 1

Properties of *Herbaspirillum* sp. MYK-B001 strain and MYK-B002 strain, and *Azospirillum* sp. MYK-B003 strain (strains deposited in the National Institute of Bioscience and Human-Technology)

| | Plant infection and symbiosis | | |
|---|---|---|---|
| Plant species | *Herbaspirillum* sp. MYK-B001 strain | *Herbaspirillum* sp. KYK-B002 strain | *Azospirillum* sp. KYK-B003 strain |
| Oryza | | | |
| O. sativa | +[1] | + | + |
| O. glaberrima | + | + | + |
| Triticum | | | |
| T. aestivum | + | + | + |
| T. dicoccum | + | + | + |
| T. durum | + | + | + |
| T. monococcum | + | + | + |
| Aegilops | | | |
| A. squarrosa | + | + | + |
| A. speltoides | + | + | + |
| Avena | | | |
| A. sativa | + | + | + |
| Secale | | | |
| S. cereale | + | + | + |

TABLE 1-continued

Properties of *Herbaspirillum* sp. MYK-B001 strain and MYK-B002 strain, and *Azospirillum* sp. MYK-B003 strain (strains deposited in the National Institute of Bioscience and Human-Technology)

| | Plant infection and symbiosis | | |
|---|---|---|---|
| Plant species | *Herbaspirillum* sp. MYK-B001 strain | *Herbaspirillum* sp. KYK-B002 strain | *Azospirillum* sp. KYK-B003 strain |
| Hordeum | | | |
| H. vulgara | + | + | + |
| Zea | | | |
| Z. mays | + | + | + |
| Sacchrum | | | |
| S. officinarum | + | + | + |
| Sorghum | | | |
| S. Bicolor | + | + | + |
| Coix | | | |
| C. lacrymajobi | + | + | + |
| Agrostis | | | |
| A. alba | + | + | + |
| A. canina | + | + | + |
| A. palustris | + | + | + |
| A. tenuis | + | + | + |
| Festuca | | | |
| F. arundinacea | + | + | + |
| F. ovina | + | + | + |
| F. o. var. duriuscula | + | + | + |
| F. Pratensis | + | + | + |
| F. fubra | + | + | + |
| F. r. var. commutata | + | + | + |
| Lolium | | | |
| L. multigirum | + | + | + |
| L. perenne | + | + | + |

[1] Infection and symbiosis confirmed

TABLE 2

Properties of *Herbaspirillum* sp. MYK-B001 strain and MYK-B002 strain, and *Azospirillum* sp. MYK-B003 strain (strains deposited in the National Institute of Bioscience and Human-Technology)

| | Plant infection and symbiosis | | |
|---|---|---|---|
| Plant species | *Herbaspirillum* sp. MYK-B001 strain | *Herbaspirillum* sp. KYK-B002 strain | *Azospirillum* sp. KYK-B003 strain |
| Poa | | | |
| P. compressa | +[1] | + | + |
| P. Pratensis | + | + | + |
| P. trivialis | + | + | + |
| Dactylis | | | |
| D. glomerata | + | + | + |
| Zoysia | | | |
| Z. japonica | + | + | + |
| Z. matrella | + | + | + |
| Z. temuifolla | + | + | + |
| Buchloe | | | |
| B. dactyloides | + | + | + |

TABLE 2-continued

Properties of *Herbaspirillum* sp. MYK-B001 strain and MYK-B002 strain, and *Azospirillum* sp. MYK-B003 strain (strains deposited in the National Institute of Bioscience and Human-Technology)

| | Plant infection and symbiosis | | |
|---|---|---|---|
| Plant species | *Herbaspirillum* sp. MYK-B001 strain | *Herbaspirillum* sp. KYK-B002 strain | *Azospirillum* sp. KYK-B003 strain |
| *Cynodon* | | | |
| C. dactylon | + | + | + |
| C. transvaalensis | + | + | + |
| *Eragrostis* | | | |
| E. curvula | + | + | + |
| *Eremochloa* | | | |
| E. ophiuroides | + | + | + |
| *Axonopus* | | | |
| A. affinis | + | + | + |
| *Paspalum* | | | |
| P. dilatatum | + | + | + |
| P. notatum | + | + | + |
| *Pennisetum* | | | |
| P. clandestinum | + | + | + |
| *Stenotaphrum* | | | |
| S. secundatum | + | + | + |
| *Phlem* | | | |
| P. pratense | + | + | + |

[1] Infection and symbiosis confirmed

The invention claimed is:

1. A pest control material, which comprises endophytic bacteria isolated from a natural plant as its main ingredient, wherein the bacteria confer pest resistance to plants of Poaceae to which the bacteria are artificially introduced, wherein the conferred pest resistance is other than resistance to diseases caused by bacteria or filamentous fungi, wherein the endophytic bacteria belong to the genus *Herbaspirillum* or the genus *Azospirillum*.

2. The pest control material according to claim 1, wherein the endophytic bacteria are one or more of the endophytic bacteria deposited in the National Institute of Advanced Industrial Science and Technology under the accession numbers FERM BP-10395, FERM BP-10447, FERM BP-7998, FERM BP-7999, and FERM BP-8000.

3. A pest control material, which comprises endophytic bacteria isolated from a natural plant as its main ingredient, wherein the bacteria confer pest resistance to plants of Poaceae to which the bacteria are artificially introduced, wherein the conferred pest resistance is other than resistance to diseases caused by bacteria or filamentous fungi, wherein the endophytic bacteria have been dispersed in a binding agent that forms a seed-coating layer.

4. A pest control material, which comprises endophytic bacteria isolated from a natural plant as its main ingredient, wherein the bacteria confer resistance to plants of Poaceae to which the bacteria are artificially introduced, and wherein the endophytic bacteria belong to the genus *Herbaspirillum* or the genus *Azospirillum*, wherein the endophytic bacteria are one or more of the endophytic bacteria deposited in the National Institute of Advanced Industrial Science and Technology under the accession numbers FERM BP-10395, FERM BP-10447, FERM BP-7998, FERM BP-7999, and FERM BP-8000.

5. A pest control method for plants of Poaceae, which comprises infecting a plant of poaceae by artificially introducing endophytic bacteria into the plant, and thus conferring pest resistance to the plant via the endophytic bacteria, wherein the conferred pest resistance is other than resistance to diseases caused by bacteria or filamentous fungi, wherein the endophytic bacteria belong to the genus *Herbaspirillum* or the genus *Azospirillum*.

6. The pest control method according to claim 5, wherein the endophytic bacteria are one or more of the endophytic bacteria deposited in the National Institute of Advanced Industrial Science and Technology under accession numbers FERM BP-10395, FERM BP-10447, FERM BP-7998, FERM BP-7999 and FERM BP-8000.

7. A pest control method for plants of Poaceae, which comprises infecting a plant of poaceae by artificially introducing endophytic bacteria into the plant, and thus conferring pest resistance to the plant via the endophytic bacteria, wherein the conferred pest resistance is other than resistance to diseases caused by bacteria or filamentous fungi, wherein the endophytic bacteria inhabit intercellular spaces in a plant, and express pest resistance in the plant.

8. A pest control method for plants of Poaceae, which comprises infecting a plant of Poaceae by artificially introducing endophytic bacteria into the plant, and thus conferring pest resistance to the plant via the endophytic bacteria, wherein the endophytic bacteria belong to the genus *Herbaspirillum* or the genus *Azospirillum*.

9. The pest control method according to claim 8, wherein the endophytic bacteria are one or more of the endophytic bacteria deposited in the National Institute of Advanced Industrial Science and Technology under the accession numbers FERM BP-10395, FERM BP-10447, FERM BP-7998, FERM BP-7999 and FERM BP-8000.

* * * * *